US006326031B1

(12) United States Patent
Hsia et al.

(10) Patent No.: US 6,326,031 B1
(45) Date of Patent: Dec. 4, 2001

(54) METHOD OF DECREASING CHOLESTEROL AND TRIGLYCERIDES LEVELS WITH A COMPOSITION CONTAINING FISH OIL, GARLIC, RUTIN, AND CAPSAICIN

(75) Inventors: Simon Houn Hsia, Foothill Ranch; David Fan, Mission Veijo, both of CA (US)

(73) Assignee: Viva Life Science, Inc., Costa Mesa, CA (US)

( * ) Notice: Subject to any disclaimer, the term of this patent is extended or adjusted under 35 U.S.C. 154(b) by 0 days.

(21) Appl. No.: 09/461,303

(22) Filed: Dec. 13, 1999

Related U.S. Application Data

(63) Continuation of application No. 08/661,088, filed on Jun. 10, 1996, now abandoned.

(51) Int. Cl.$^7$ .................................................... A61K 35/60

(52) U.S. Cl. .................... 424/523; 435/554; 435/725; 435/754; 435/700; 426/73; 426/599; 426/601; 426/602; 426/648

(58) Field of Search ..................................... 424/523, 554, 424/725, 754, 760; 426/73, 599, 601, 602, 648

(56) References Cited

U.S. PATENT DOCUMENTS

| 4,680,313 | 7/1987 | Iwai . |
| 4,789,687 | 12/1988 | Iwai . |
| 5,578,307 | 11/1996 | Wunderlich et al. . |

FOREIGN PATENT DOCUMENTS

WO 87/03899    7/1987   (WO) .

OTHER PUBLICATIONS

Capsaicin Lowers Plasma Cholesterol and Triglycerides of Lagomorphs, J.A. Negulesco et al, Artery 12(5):301–311(1983).
The Merck Index, 1996, p. 1528.
Should 'Eat Fish' Advice be Thrown Overboard?,Tufts University Diet & Nutrition Letter, Jun. 1995, vol. 13, No. 4., p. 1–2.
Elwood et al., Inter–relationships between haemostatic tests and the effects of some dietary determinants in the Caerphilly cohort of older men, Blood Coagul Fibrinolysis 4 (4). 1993. 529–536.
A.C. Rustan, et al., Eicosapentaenoic Acid Reduces Hepatic Synthesis and Secretion of Triacylglycerol by decreasing the Activity of Acyl–coenzyme A:1,2–Diacylglycerol Acyltransferase, 29 J. Lipid. Res. 1417 (1988).
A.C. Rustan, et al., Eicosapentaenoic Acid Inhibits Cholesterol Esterification in Cultured Parenchymal Cells and Isolated Microsomes from Rat Liver, 263 J. Biol. Chem. 8126 (1988).

Adler, Allen J. and Holub, Bruce J., Effect of Garlic and Fish–Oil Supplementation on Serum Lipid and Lipoprotein Concentrations in Hypercholesterolemic Men. 65 Am. J. Clin. Nutr. 445 (1997).
Kawada, Teruo, et al., Effects of Capacin on Lipid Metabolism in Rats Fed a High Fat Diet, 116 J. Nutr. 1272 (1986).
Sambaiah, K. and Satyanarayana, N. Hypercholesteremic Effect of Red Pepper and Capsaicin, 18 Indian J. Exp. Biol. 898 (1980).
Schmitt, A., et al., Prevention by α–tocopherol and Rutin of Glutathione and ATP Depletion Induced by Oxidized LDL in Cultured Endothelial Cells, 116 Brit. J. Pharm. 1985 (1995).
Shimoi, K., et al., Protection by Alpha–G–Rutin, A Water–Soluble Antioxidant Flavonoid, Against Renal Damage in Mice Treated with ferric Nitrilotriacetate, 88 Japanese J. Cancer Res. 453 (1997).
Ortolani, O., et al., Protection from ischemia–Reperfusion Damage in Patients with Stroke: The Role of Rutin and GSH, 27 Transplantation Proc. 2877 (1995).
Morcos, N.C., Modulation of Lipid Profile by Fish Oil and Garlic Combination, 89 J. Natl. Med. Ass'n. 673 (1997).
Harris, William S, n–3 Fatty Acids and Lipoproteins: Comparison of Results from Human and Animal Studies, 31 Lipids 243 (1996).
Kris–Etherton, Penny M., et al. Efficacy of multiple dietary therapies in reducing cardiovascular disease risk factors, Am. J. Clin. Nutr. 1997:65;560–1.
Stone, Neil J. M.D., Fish Consumption, Fish Oil, Lipids, and Coronary Heart Disease, AHA Science Advisory, vol. 94, No. 9 Nov. 1, 1996:2337–2340.
Brosche, T., Platt, D., Dorner, H., The Effect of a Garlic Preparation on the Composition of Plasma Lipoproteins and Erythrocyte Membranes in Geriatric Subjects, Brit. J. Clinic. Pract., vol. 44, No. 8, pp. 12–19 (Aug. 1990).
Kiesewetter, H., Jung, F., Mrowietz, C., Pindur, G., Heiden, M., Wenzel, E., Effects of Garlic on Blood Fluidity and Fibrinolytic Activity: a randomised, placebo–controlled, double–blind study, Brit. J. Clinic. Pract., vol. 44, No. 8, pp. 24–29 (Aug. 1990).
Auer, W., Eiber, A., Hertkorn, E., Hoehfeld, E., Koehrle, U., Lorenz, A., Mader, F., Merx, W., Otto, G., Schmid–Otto, B., Taubenheim, H., Hypertension and Hyperlipidaemia: garlic helps in mild cases, Brit. J. Clinic. Pract., vol. 44, No. 8, pp. 3–6 (Aug. 1990).
Manach, C., Morand, C., Texier, O., Favier, M–L, Agullo, G., Demigne, Ch., Regerat, F., Remesy, C., Quercetin Metabolites in Plasma of Rats Fed Diets Containing Rutin or Quercetin, J. of Nutr., vol. 125, pp. 1911–1922.

(List continued on next page.)

Primary Examiner—Irene Marx
(74) Attorney, Agent, or Firm—Lyon & Lyon LLP

(57) ABSTRACT

The present invention relates to nutritional supplements to the human diet used to increase levels of HDL, and decrease levels of O-LDL, cholesterol, and triglycerides in human blood plasma. More specifically, the present invention teaches novel nutritional supplements which contain a novel combination of fish oil, garlic, rutin, and capsaicin, as well as methods of preparing the nutritional supplements.

11 Claims, 1 Drawing Sheet

OTHER PUBLICATIONS

Figure 1:
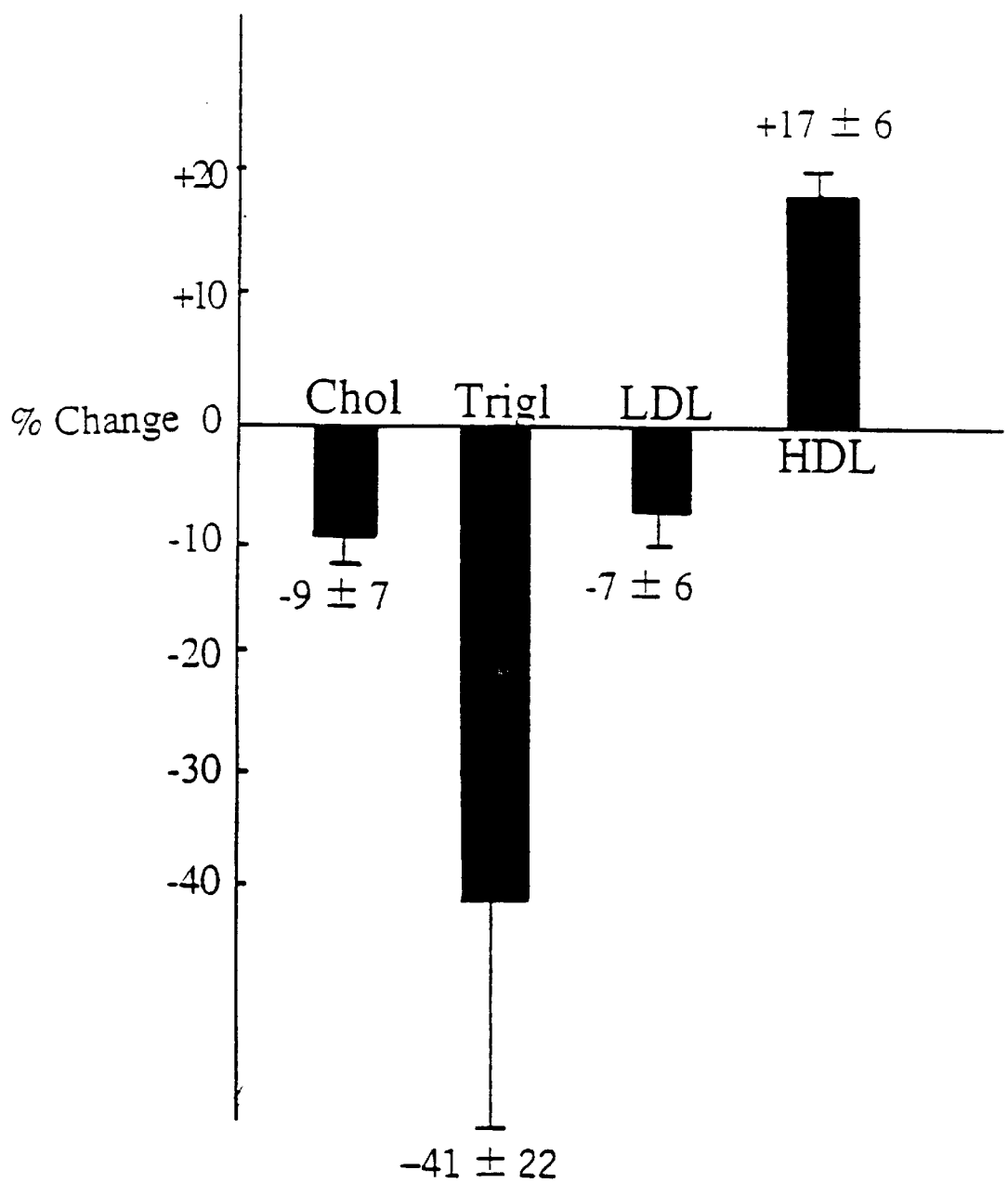

Gerster, H., The Use of n–3 PUFAs (Fish Oil) in Enteral Nutrition., Internat. J. Vit. Nutr. Res., 65:3–20 (1995).

Levy, E., et al., Beneficial effects of fish–oil supplements on lipids, lipoproteins, and lipoprotein lipase in patients with glycogen storage disease type $1^{1-3}$, I. Am. J. Clin. Nutr., 57:922–29 (1993).

Effect of Fish Oil/ Garlic on Lipid Profile

METHOD OF DECREASING CHOLESTEROL AND TRIGLYCERIDES LEVELS WITH A COMPOSITION CONTAINING FISH OIL, GARLIC, RUTIN, AND CAPSAICIN

CROSS-REFERENCE TO RELATED APPLICATION

This is a continuation application of U.S. application Ser. No. 08/661,088, filed Jun. 10, 1996 now abandoned.

BACKGROUND OF THE INVENTION

1. Field of the Invention

The present invention provides a novel composition for preventing cardiovascular diseases in the human system, and more specifically to nutritive compositions containing fish oil, garlic, rutin, and capsaicin that reduce the levels of triglycerides, cholesterol, and low density lipoprotein (LDL) in the human blood serum, and increase the levels of high density lipoprotein (HDL) in human blood serum.

2. Background of the Invention

In the few years, scientific literature has provided strong evidence for a bona fide link between micronutrient compositions (such as vitamins, minerals, fish oils, and plant extracts) and cardiovascular disease. For humans of high risk for cardiovascular diseases, realizing an appreciable reduction in the levels of high cholesterol, triglycerides, low density lipoprotein (LDL) in their blood serum is known to be important for reducing the risk of cardiac diseases. It is also known that effecting an increase in the levels of high density lipoprotein (HDL) also provides a significant decrease to the risk of cardiac diseases.

Cardiovascular disease resulting from the buildup of arterial plaque is known to be a leading cause of illness and death in humans. Arterial plaque is caused by precipitous material formed chiefly of oxidized low density lipoprotein (O-LDL). The buildup of plaque in the form of O-LDL in the arteries is understood to be a factor in ischemic heart disease. Free radical oxidants, many of which come from naturally occurring sources such as sun exposure, metabolism of certain nutrients, exercise, or are otherwise often observed in persons suffering from diabetes and high blood pressure, act to oxidize LDL into its deleterious form, O-LDL. Free radical "scavengers" such as vitamins A, E, C, and selenium are believed to react with these oxidants and render them incapable of oxidation. The inhibitory action of these antioxidants thus inhibits the formation of O-LDL, thereby lowering the levels of arterial plaque deposits in blood vessels. In contrast, the presence of high density lipoprotein (HDL) in the body is understood to have beneficial health effects. Specifically, HDL is known to be more soluble form of lipoprotein, hence its presence does not significantly contribute to the formation of arterial plaque. In addition, it is known that HDL is able to absorb plaque material and may thus directly reduce the amount of arterial plaque.

3. Description of Prior Art

Essential fatty acids (EFAs) are naturally occurring unsaturated fatty acids with a chain length of 18, 20, or 22 carbon atoms. These EFAs cannot be synthesized by the body, hence, dietary intake of EFAs is required. Two fatty acids which fall within the family of EFAs are eicosapantaenoic acid (EPA) and docosahexaenoic acid (DHA), both of which are commonly found in fish oils. Epidemiological observations indicate that fish oils reduce platelet aggregation and serum triglycerides which may reduce the risk of myocardial infarction, hypertension, antherosclerosis, and certain types of cancer. [Gerster, H., *Internat. J. Vit. Nutr. Res.*, 65:3–20 (1994)]. Specifically, it has been shown that EPA and DHA derived from fish oils play important structural roles in membranes of most cells, and influence the fluidity of the cell membranes as expressed by decreased whole-blood viscosity and increased erythrocyte flexibility and deformability [Gerster, cited above]. In addition, EFAs such as EPA and DHA are known precursors of eiconsanoids—a class of compounds which includes prostanoids such as prostaglandins and thromboxanes, leukotrienes, and hydroxy fatty acids. Eiconsanoids are known are known to affect platelet aggregation, permeability and tone of the blood vessel walls, blood pressure, and inflammatory immune reactions. [Gerster, cited above].

Fish oil dietary supplementation is known to have other beneficial health effects. Glycogen storage disease is an inherited disorder, and is often complicated by severe hyperlipoproteinemia and hypercholesterolemia, which increase the risk of premature atherosclerosis and cadiovascular diseases. It has been reported that patients suffering from glycogen storage disease that received 10 grams of fish oil for 3 months experienced a significant decrease in levels of triglycerides in the blood serum (−49%) and cholesterol levels in the blood serum (−23%), and a reduction in LDL levels in the blood serum (−40%), and a significant increase in HDL levels in the blood serum (+30%). [Levy, E., et al., *I. Am. J. Clin. Nutr.*, 57:922–29 (1993)].

Garlic powder has been proposed to have a number of valuable benefits to the human body as a preventative against cardiovascular diseases. For example, daily ingestion of garlic leads to reduced levels of lipids in human blood serum, increased fibrinolysis and tissue plasminogen activator (t-PA) activity, and decreased plasma fibrogen viscosity, each of which may lessen the likelihood of cardiovascular disease. [Brosche, T. et al., *British J. Clin. Practice, Supp.* 69:12–19 (1990); Kiesewetter H. et al., *British J. Clin. Practice, Supp.* 69:24–29 (1990)]. In addition, the daily ingestion of garlic is known to reduce the total levels of cholesterol and triglycerides in human serum, as well as reduce blood pressure peripheral vasodilation. [Auer, W. et al., *British J. Clin. Practice, Supp.* 69:3–6 (1990)].

Flavonoids are secondary metabolites which are found in edible plants and foodstuffs derived from plants. Flavonoids are widely recognized as having antiallergic, antiflammatory, antiviral, antiproliferative and anticarcinogenic activities. [Manach, C., et al. *J. Nutr.*, 125:1911–22 (1995)]. Among flavonoids, flavonols occur most abudantly in plants as possess most of these biological properties. [Manach, cited above]. Flavonols naturally occur as O-glycides, typically having a sugar moiety bound at the C-3 position. Rutin is the principal glycoside form of quercetin, the most abundant flavonol in fruits and vegetables.

Capsaicin is a prominent chemical entity in plants of the Capsicum genus, which include chili peppers, red pepper, and paprika. Capsaicin is actually a class of compounds of branched- and straight-chain alkyl vanillylamides. The antimicrobial and analgesic properties of capsaicin have been known for centuries. In addition, capsaicin-containing products have been used to treat rheumatoid arthritis, osteoarthritis, diabetic neuropathy, postherpetic neuralgia, postmastectomy pain syndrome, cluster headache, and reflex sympathetic syndrome. [Cordell, G. and Araujo, O., *Ann. Pharm.*, 27:330–36 (1993)].

Although compositions used to reduce the risks of cardiovascular disease are known, the present invention comprises a novel combination of fish oil, garlic, rutin, and capsaicin, which achieve this purpose. As such, there remains a need in the art for novel compositions like those of the present invention which may be used to treat or prevent cardiovascular disease and disorders.

SUMMARY OF THE INVENTION

The present invention relates to the use of nutritional supplement compositions to overcome the nutritional deficiencies typically associated with the normal Western diet. The compositions of the present invention are obtained by combining fish oil, garlic powder, rutin, and capsaicin, Specifically, the present invention relates to the daily co-administration of one preparation of fish oil, preferably as a single fish oil lozenge, and a preparation comprised of garlic powder, rutin, and capsaicin, preferably in a single lozenge.

It is therefore an object of the invention to provide nutritious and safe compositions for human consumption as dietary supplements that contain fish oil, garlic powder, rutin, and capsaicin.

It is another object to provide novel compositions which will increase the levels of HDL in human blood serum.

It is a further object of the invention to provide compositions which will decrease levels of O-LDL in human blood serum.

It is still another object of the invention to provide compositions which will reduce the levels of cholesterol and triglycerides in human blood serum.

The increase of HDL and the reduction of cholesterol and O-LDL should act to reduce the risk of heart disease in humans. Therefore, it is another object of the present invention to provide for the reduction of the risk of cardiovascular disease by daily administration of the compositions of the invention.

DETAILED DESCRIPTION OF THE INVENTION

Daily does of the compositions of the present invention are aimed at reducing the rate of occurrence of heart disease and are comprised of: (1) fish oil; (2) garlic powder; (3) rutin; (4) capsaicin. More specifically, the compositions of the present invention are a combination of a fish oil preparation, preferably in the form of a single fish oil lozenge, and a preparation comprised of garlic powder, rutin, and capsaicin, preferably in the form of a single lozenge which is co-administered with the fish oil lozenge. The preferred weight of the fish oil lozenge is between about 500 mg and about 1500 mg, preferably about 1000 mg. The preferred weight of the garlic lozenge is between about 400 mg and about 1000 mg, and most preferably about 700 mg.

The fish oil preparation component of the compositions of the present invention may be available from commercial sources. [Arista, Pharmachem]. EPA and DHA are the active moieties of the fish oil preparation. The fish oil preparation of the present invention comprises EPA in the amount of about 250 mg to about 350 mg, and most preferably about 300 mg. The remainder of the fish oil preparation comprises from about 150 mg to about 250 mg of DHA, and preferably about 200 mg of DHA. The total weight of the fish oil preparation of the present invention is from about 500 mg to about 1500 mg, and preferably about 1000 mg per fish oil lozenge when in the form of a single fish oil lozenge.

The garlic powder used in the garlic powder, rutin, and capsaicin preparation component of the compositions of the present invention may be obtained from commercially available sources. [Extracts, Ashland, Pure-Gar]. In addition, it is preferable to use a deodorized and aged form of garlic powder. A pharmaceutically acceptable form of garlic powder used in the compositions of the present invention comprises, by weight, from about 100 mg to about 700 mg, and more preferably about 175 mg to about 650 mg, and most preferably 500 mg of deodorized and aged garlic powder per garlic/rutin/capsaicin lozenge when in the form of a single lozenge.

The rutin which is employed in the garlic powder, rutin, and capsaicin preparation component of the compositions of the present invention may also be obtained from commercially available sources. [Westco Chemical, Freeman Industries, Inc.]. The rutin component of the garlic powder, rutin, and capsaicin preparation comprised, by weight, from about 10 mg to about 150 mg, and most preferably about 100 mg.

Capsaicin which is used in the compositions of the present inventions may be commercially obtained. [AllChem, Good Hope Botanicals]. When employed in the garlic powder, rutin, capsaicin preparation of the present invention, the capsaicin component of the compositions of the present invention comprises, by weight, from about 20 mg to about 150 mg, and most preferably about 100 mg of capsaicin.

The garlic powder, rutin, and capsaicin components are admixed in the same preparation. This preparation is co-administered with the fish oil preparation—the two preparations comprising the compositions of the present invention.

These preparations may be made by conventional methods. To prepare the compositions of the invention, the above-described fish oil and garlic powder/rutin/capsaicin preparations are combined as the active ingredient in intimate admixture with a suitable carrier according to conventional compounding techniques. This carrier may take a wide variety of forms depending upon the form of preparation desired for administration, e.g., oral, sublingual, nasal, or parenteral.

In preparing the compositions in oral dosage form, any of the usual pharmaceutical media may be employed. For oral liquid preparations (e.g., suspensions, elixirs, and solutions), media containing for example, water, oils, alcohols, flavoring agents, preservatives, coloring agents and the like may be used. Carriers such as starches, sugars, diluents, granulating agents, lubricants, binders, disintegrating agents, and the like may be used to prepare oral solids (e.g., powders, capsules, pills, tablets, and lozenges). Lozenges are a preferred oral dosage form. Controlled release forms may also be used. Because of their ease in administration, lozenges, tablets, pills, and capsules represent the most advantageous oral dosage unit form, in which case solid pharmaceutical carriers are obviously employed. If desired, tablets may be sugar coated or enteric coated by standard techniques.

Examples of these additional inactive components which provide for easier oral administration include but are not limited to lemon bioflavonoids [Botanical International, Freeman], parsely powder d-alpha tocopherol, bee's wax, lecithin, gelatin, purified water, and glycerin. These compounds may be used in creating the lozenges of the novel nutritional supplements.

For parenteral products, the carrier will usually comprise sterile water, although other ingredients may be included, e.g., to aid solubility or for preservation purposes. Injectable suspensions may also be prepared, in which case appropriate liquid carriers, suspending agents, and the like may be employed.

A preferred method for using the present invention is for the user to ingest, daily from about 4 to 8 lozenges of the fish oil preparation, most preferably about 6 lozenges of the fish oil preparation, together with from about 3 to 5 lozenges of the garlic powder, capsaicin and rutin preparation, and most preferably 4 lozenges of the garlic powder, capsaicin and rutin preparation.

The following examples illustrate the preferred embodiments of the present invention. These examples are illustrative only, and do not purport to limit the invention in any fashion.

EXAMPLE 1

The effect of the present invention on the human lipid profile was measured. A double blind study carried out at the University of California at Irvine Medical School showed that the proper use of the present invention provides for the following effects in human blood serum: (1) a significant reduction in triglyceride levels; (2) a significant decrease in cholesterol and LDL; and (3) a significant increase in the levels of HDL.

The protocol followed during this investigation was as follows. Ten subjects participated in a month-long study wherein each subject ingested ten lozenges for each day of the study. The placebo group used 10 nonactive lozenges each day for one month, and the active group ingested 10 lozenges of the present invention each day for one month. Each subject ingested three fish oil lozenges and two garlic powder/rutin/capsaicin lozenges (twice daily) for a total daily ingestion of ten lozenges. The identity of the lozenge was unknown by the subjects, and to the examiner (i.e., a double blind study). Blood serum (approximately 4 cc) was collected at the starting time and again after the completion of one month of usage. A fasting lipid profile was conducted on the plasma samples using a lipid fractionation panel automated system. [Hewlett-Packard Co.]. In addition, measurements of electrolytes (including calcium ion) and glucose levels were made using the Chem automated system. [Hewlett-Packard Co.]. The results were compared using statistical analytical methods and are shown in the attached FIG. 1.

These results demonstrate a reduction in plasma triglyceride concentration of 41% in comparison to the placebo. In addition, the cholesterol levels showed a 9% reduction, the LDL levels showed a 7% reduction, and the HDL levels showed a 17% increase.

These data provide the basis for evaluating the effectiveness of the present invention in causing an increase in human serum HDL levels and a decrease in the levels of serum cholesterol, triglycerides, and low density lipoprotein (LDL).

EXAMPLE 2

The following example provides a preferred composition of the present invention. The composition is provided as two separate preparations: lozenge A (fish oil) and lozenge B (garlic, capsaicin, and rutin). The proper daily dosage is six of lozenge A and four of lozenge B (in other words, three of lozenge A and two of lozenge B taken twice daily for a total of ten lozenges).

| Ingredient | Weight |
| --- | --- |
| Lozenge A | 1000 mg |
| Fish Oil | 1000 mg |
| Lozenge B | 700 mg |
| Garlic Powder | 487 mg |
| Capsaicin | 53 mg |
| Rutin | 27 mg |
| lemon bioflavonoid | 23 mg |
| parsley powder | 110 mg |

EXAMPLE 3

The following example provides a preferred composition of the present invention. The composition is provided as two separate preparations: Lozenge A (fish oil) and Lozenge B (garlic, capsaicin, rutin). The proper dosage is six capsules of Lozenge A each day and four capsules of Lozenge B (in other words, three of lozenge A and two of lozenge B taken twice daily for a total of ten lozenges).

| Ingredient | Weight |
| --- | --- |
| Lozenge A | 950 mg |
| Fish Oil | 950 mg |
| Lozenge B | 700 mg |
| Garlic Powder | 600 mg |
| Capsaicin | 50 mg |
| Rutin | 50 mg |

EXAMPLE 4

The following example provides a preferred composition of the present invention. The composition is provided as a single preparation. The proper dosage is five capsules of the lozenge taken twice each day.

| Ingredient | Weight |
| --- | --- |
| fish oil* | 570 mg |
| garlic powder | 194 mg |
| rutin | 11 mg |
| capsaicin | 21 mg |
| lemon bioflavonoids | 11 mg |
| parsley powder | 38 mg |
| d-alpha tocopherol | 5 mg |
| bee's wax | 75 mg |
| lecithin | 75 mg |
| gelatin | 255 mg |
| purified water | 10 mg |
| glycerin | 170 mg |

*fish oil in the form of 300:200 of EPA:DHA

Numerous modifications and variations of the present invention are included in the above-identified specification and are expected to be obvious to one of skill in the art. It is also intended that the present invention cover modifications and variations of the compositions and method for using them to accomplish their claimed uses within the scope of the appended claims and their equivalents.

We claim:

1. A method to decrease the levels of cholesterol and triglycerides in human blood plasma comprising:

orally administering to humans in need of reduction of plasma triglycerides and cholesterol a daily dose of a nutritional supplement comprising in combination approximately 2000 mg to approximately 12000 mg fish oil, which comprises approximately 1000 mg to 2800 mg EPA and approximately 600 mg to 2000 mg DHA, approximately 300 mg to approximately 3500 mg garlic powder, approximately 30 mg to approximately 750 mg rutin, and approximately 60 mg to approximately 750 mg capsaicin.

2. The method of claim 1 in which the daily dose of fish oil is approximately 3000 mg to approximately 9000 mg.

3. The method of claim 1 in which the daily dose of fish oil is approximately 4000 mg to approximately 8000 mg.

4. The method of claim 1 in which the daily dose of fish oil is approximately 6000 mg.

5. The method of claim 1 in which the daily dose of garlic powder is approximately 400 mg to approximately 2800 mg.

6. The method of claim 1 in which the daily dose of garlic powder is approximately 1500 mg to approximately 2000 mg.

7. The method of claim 1 in which the daily dose of garlic powder is approximately 2000 mg.

8. The method of claim 1 in which the daily dose of garlic powder is approximately 40 mg to approximately 600 mg.

9. The method of claim 1 in which the daily dose of capsaicin is approximately 80 mg to approximately 600 mg.

10. The method of claim 1, wherein the levels of O-LDL in human blood plasma is reduced as a result of administering the nutritional supplement.

11. The method of claim 1, wherein the levels of HDL in human blood plasma is increased as a result of administering the nutritional supplement.

* * * * *